(12) United States Patent
Mauch et al.

(10) Patent No.: US 8,377,083 B2
(45) Date of Patent: *Feb. 19, 2013

(54) PERCUTANEOUS METHODS AND APPARATUS FOR CREATING NATIVE TISSUE VENOUS VALVES

(75) Inventors: Kevin Mauch, Windsor, CA (US); Douglas Green, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 273 days.

This patent is subject to a terminal disclaimer.

(21) Appl. No.: 12/767,932

(22) Filed: Apr. 27, 2010

(65) Prior Publication Data

US 2011/0264127 A1 Oct. 27, 2011

(51) Int. Cl.
*A61B 17/32* (2006.01)
*A61M 25/10* (2006.01)

(52) U.S. Cl. ... 606/159; 606/185; 606/194; 604/103.08; 128/898

(58) Field of Classification Search ............... 606/159, 606/167, 185, 191, 192, 194; 604/96.01, 604/103.06, 103.08; 623/1.11, 1.13, 2.11, 623/2.13, 23.64, 901, 903, 904, 909, 910, 623/915, 916, 920; 128/898

See application file for complete search history.

(56) References Cited

U.S. PATENT DOCUMENTS

| | | | | |
|---|---|---|---|---|
| 5,464,395 A | * | 11/1995 | Faxon et al. | 604/103.02 |
| 5,697,944 A | * | 12/1997 | Lary | 606/159 |
| 6,165,187 A | | 12/2000 | Reger | |
| 6,902,576 B2 | | 6/2005 | Drasler et al. | |
| 7,008,411 B1 | * | 3/2006 | Mandrusov et al. | 604/164.01 |
| 7,029,483 B2 | | 4/2006 | Schwartz | |
| 7,150,738 B2 | * | 12/2006 | Ray et al. | 604/103.01 |
| 7,517,352 B2 | * | 4/2009 | Evans et al. | 606/192 |
| 7,955,346 B2 | * | 6/2011 | Mauch et al. | 606/159 |
| 2011/0264128 A1 | * | 10/2011 | Mauch et al. | 606/170 |

* cited by examiner

*Primary Examiner* — Kathleen Sonnett
*Assistant Examiner* — Sarah W Aleman (57) ABSTRACT

Percutaneous methods and apparatus for forming a venous valve from autologous tissue by creating at least one subintimal longitudinal dissection that forms at least one flap of intimal tissue are disclosed. In one method, a balloon catheter having a dissecting blade mounted thereon is delivered to a target site where a new venous valve is to be created. The balloon is inflated to deploy the blade against the vein wall, and the catheter is longitudinally translated such that the blade dissects a subintimal layer of the vein wall. The balloon is subsequently deflated such that the blade pulls a flap of the dissected tissue towards the vein lumen, thereby creating a leaflet and corresponding pocket/sinus in the vein that collectively act as a monocuspid venous valve. Methods of forming new bicuspid and tricuspid venous valves utilizing two or three dissecting blades mounted on the balloon are also disclosed.

16 Claims, 9 Drawing Sheets

PERCUTANEOUS METHODS AND APPARATUS FOR CREATING NATIVE TISSUE VENOUS VALVES

FIELD OF THE INVENTION

The invention relates to apparatus and methods for percutaneously creating a one-way venous valve in vivo from autologous tissue.

BACKGROUND OF THE INVENTION

Venous valves are found within native venous vessels and are used to assist in returning blood back to the heart in an antegrade direction from all parts of the body. The venous system of the leg includes the deep venous system and the superficial venous system, both of which are provided with venous valves that are intended to direct blood toward the heart and prevent backflow or retrograde flow, which can lead to blood pooling or stasis in the leg in the setting of incompetent valves. Incompetent valves can also lead to reflux of blood from the deep venous system to the superficial venous system and the formation of varicose veins. Superficial veins, which include the greater and lesser saphenous veins, have perforating branches in the femoral and popliteal regions of the leg that direct blood flow toward the deep venous system and generally have a venous valve located near the junction with the deep system. Deep veins of the leg include the anterior and posterior tibial veins, popliteal veins, and femoral veins. Deep veins are surrounded in part by musculature tissue that assists in generating flow due to muscle contraction during normal walking or exercising. Veins in the lower leg have a static pressure while standing of approximately 80-90 mm Hg that may reduce during exercise to 60-70 mm Hg. Despite exposure to such pressures, the valves of the leg are very flexible and can close with a pressure drop of less than one mm Hg.

Figure 1A:
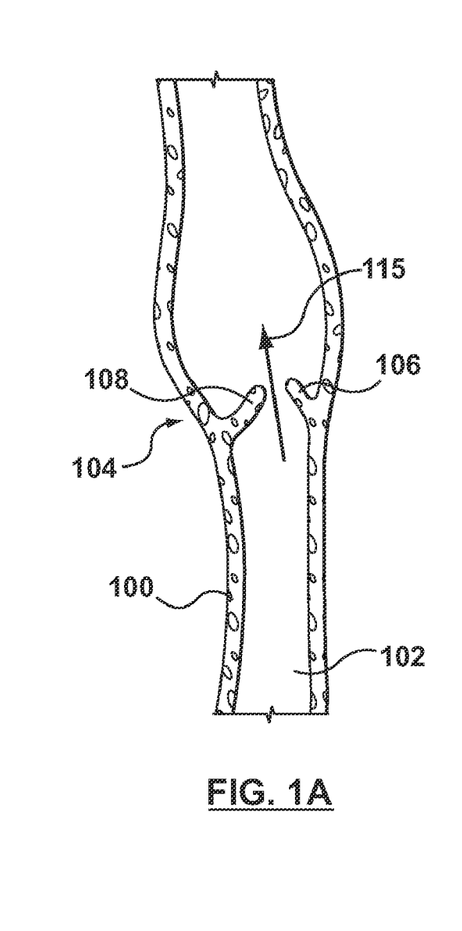
FIGS. 1A-1B are schematic representations of blood flow through a healthy valve within a vein.
Figures 1B, 2:
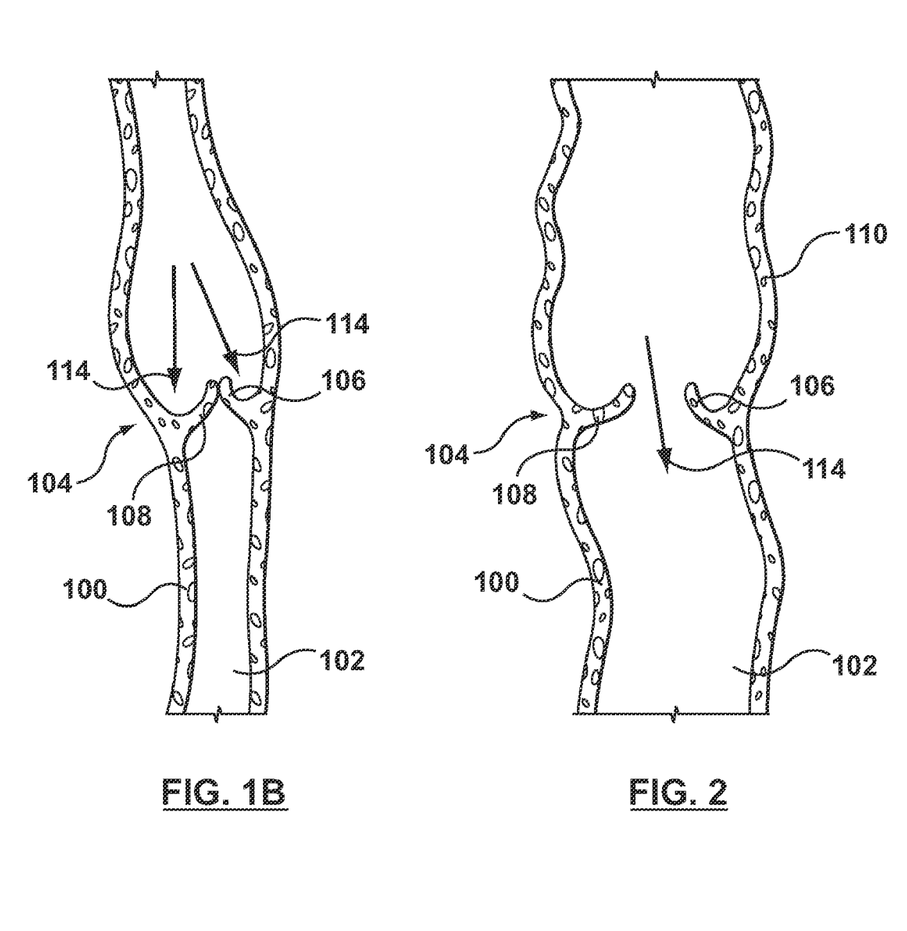
FIG. 2 is a schematic representation of blood flow through an incompetent valve within a vein.

FIGS. 1A-1B are schematic representations of blood flow through a healthy native valve 104 within a vein 100. Venous valve 104 controls blood flow through lumen 102 of vein 100 via leaflets 106, 108. More particularly, venous valve 104 opens to allow antegrade flow 112 through leaflets 106, 108 as shown in FIG. 1A. Venous valve 104 closes to prevent backflow or retrograde flow 114 through leaflets 106, 108 as shown in FIG. 1B.

Veins typically in the leg can become distended from prolonged exposure to excessive pressure and due to weaknesses found in the vessel wall causing the natural venous valves to become incompetent leading to retrograde blood flow in the veins. Such veins no longer function to help pump or direct the blood back to the heart during normal walking or use of the leg muscles. As a result, blood tends to pool in the lower leg and can lead to leg swelling and the formation of deep venous thrombosis, phlebitis, and varicose veins. The formation of thrombus in the veins can further impair venous valvular function by causing valvular adherence to the venous wall with possible irreversible loss of valvular function. Continued exposure of the venous system to blood pooling and swelling of the surrounding tissue can lead to post phlebitic syndrome with a propensity for open sores, infection, and may lead to possible limb amputation.

Chronic Venous Insufficiency (CVI) occurs in patients that have either deep and/or superficial venous valves of their lower extremities (below their pelvis) that have failed or become incompetent due to congenital valvular abnormalities and/or pathophysiologic disease of their vasculature. As a result, these patients suffer from varicose veins, swelling and pain of the lower extremities, edema, hyper pigmentation, lipodermatosclerosis, and deep vein thrombosis (DVT). Such patients are at increased risk for development of soft tissue necrosis, ulcerations, pulmonary embolism, stroke, heart attack, and amputations.

FIG. 2 is a schematic representation of blood flow through an incompetent venous valve. Retrograde flow 114 leaks through venous valve 104 creating blood build-up that eventually may destroy the venous valve and cause a venous wall bulge 110. More specifically, the vessel wall of vein 100 expands into a pouch or bulge, such that the vessel has a knotted appearance when the pouch is filled with blood—a varicose vein. The distended vessel wall area may occur on the outflow side of the valve above leaflets 106, 108 as shown in FIG. 2, and/or on the inflow side of the valve below leaflets 106, 108. After a vein segment becomes incompetent, the vessel wall dilates such that the fluid velocity decreases within the incompetent vein segment, which may lead to flow stasis and thrombus formation in the proximity of the venous valve.

Repair and replacement of venous valves presents a formidable problem due to the low blood flow rate found in native veins, the very thin wall structure of the venous wall and the venous valve, and the ease and frequency of which venous blood flow can be impeded or totally blocked for a period of time. Surgical reconstruction techniques used to address venous valve incompetence include venous valve bypass using a segment of vein with a competent valve, venous transposition to bypass venous blood flow through a neighboring competent valve, and valvuloplasty to repair the valve cusps. These surgical approaches may involve placement of synthetic, allograft and/or xenograft prostheses inside of or around the vein. However, such prostheses have not been devoid of problems leading to thrombosis and/or valve failure due to leaflet thickening/stiffening, non-physiologic flow conditions, non-biocompatible materials and/or excessive dilation of the vessels with a subsequent decrease in blood flow rates.

Percutaneous methods for treatment of venous insufficiency are being studied, some of which include placement of synthetic, allograft and/or xenograft prosthesis that suffer from similar problems as the surgically implanted ones discussed above.

In addition, venous valve formation from autologous tissue has been disclosed in U.S. Pat. No. 6,902,576 to Drasler et al. Drasler et al. suggests use of autologous tissue with blood contact of an endothelial layer to eliminate biocompatability issues and also alleviate thrombus formation due to low flow. However, methods of in situ venous valve formation according to Drasler et al. are surgical in nature and involve reshaping a distended, diseased vein, which carries with it the risk of rupture or tearing of the thin-walled structure, or thrombosis because of extensive surgical resection.

In view of the foregoing, there exists a need for methods and apparatus to restore normal venous circulation to patients suffering from venous valve insufficiency, wherein the methods and apparatus may be used in percutaneous, minimally invasive procedures. Further, such percutaneous methods and apparatus should attend to biocompatibility and thrombosis issues that current approaches do not adequately address.

BRIEF SUMMARY OF THE INVENTION

Embodiments hereof are directed to percutaneous methods and apparatus for creating monocuspid, bicuspid, and tricuspid venous valves from autologous tissue. One method disclosed herein includes obtaining percutaneous access to the lumen of a vein and tracking a guidewire to a target location within the vein lumen where a venous valve is to be created. A balloon catheter having at least one dissecting blade coupled to the balloon is advanced over the guidewire to the target location in an antegrade manner, i.e., in the direction of antegrade blood flow. The balloon is inflated to deploy the dissecting blade against the vein wall. The balloon catheter is longitudinally translated such that the dissecting blade penetrates into the vein wall and forms a subintimal longitudinal dissection where at least intimal tissue of the vein wall is separated from remaining tissue of the vein wall. The balloon is subsequently deflated such that the dissecting blade directs the intimal and/or medial tissue from the remaining tissue of the vein wall into the lumen of the vein, simultaneously forming a flap of tissue and a sinus between the flap and the remaining tissue of the vein wall. The flap and the sinus constitute at least a portion of the venous valve.

Embodiments hereof are also directed to an apparatus for creating a venous valve from autologous tissue, the apparatus including a balloon catheter having a balloon at a distal end thereof and at least one dissecting blade coupled to the balloon. A distal end of the blade is coupled to the balloon and a proximal end of the blade is radially spaced from the balloon. The proximal end of the blade includes at least one lateral cutting edge operable to cut within a vein wall to form a subintimal longitudinal dissection of the vein wall that separates at least intimal tissue from remaining tissue of the vein wall.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments hereof are now described with reference to the figures, wherein like reference numbers indicate identical or functionally similar elements. The terms "distal" and "proximal" are used in the following description with respect to a position or direction of the balloon catheter and dissecting blade relative to the treating clinician. "Distal" or "distally" are a position distant from or in a direction away from the clinician. "Proximal" and "proximally" are a position near or in a direction toward the clinician. With reference to venous valves and/or the flaps of tissue that form a venous valve, the term "proximal" refers to an end or portion in a direction toward the heart by way of blood flow path while the term "distal" refers to an end or portion in a direction away from the heart by way of blood flow path.

The following detailed description is merely exemplary in nature and is not intended to limit the invention or the application and uses of the invention. Although the description of the invention is in the context of treatment of blood vessels such as the deep and superficial veins of the leg, the invention may also be used in any other body passageways where it is deemed useful. Furthermore, there is no intention to be bound by any expressed or implied theory presented in the preceding technical field, background, brief summary or the following detailed description.

Figure 3:
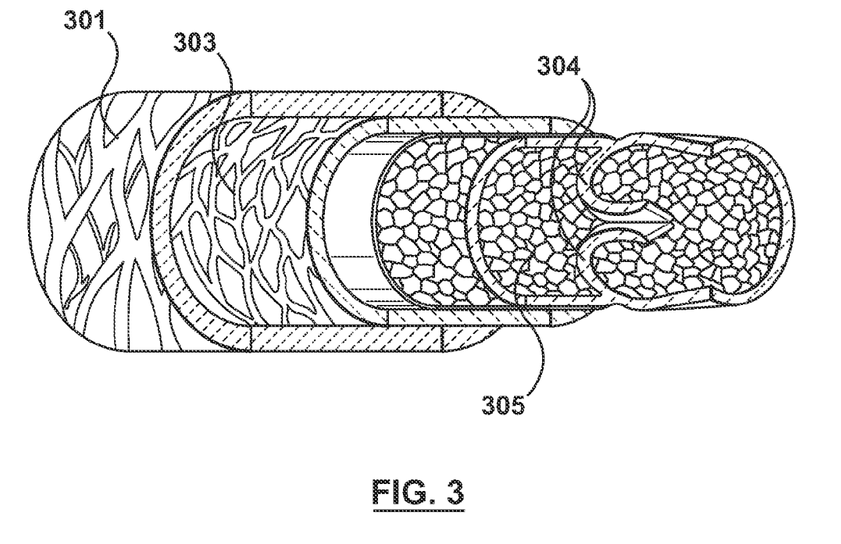
FIG. 3 is a sectional view of the anatomy of a healthy vein and valve thereof.

FIG. 3 depicts a sectional view of the anatomy of a vein wall, which for purposes of this description is shown to consist essentially of an outside layer 301, a middle layer 303 and an inside layer 305. Outer layer 301, or adventitia, is made of collagen, vasa vasorum and nerve cells. Middle layer 303, or media, is made of smooth muscle cells, whereas inner layer 305, or intima, is made up of endothelial cells. The endothelium provides a nonthrombogenic surface for flowing blood. Venous valve 304 having two leaflets is formed from folds of the inner or intimal layer such that both upstream and downstream blood contacting surfaces of valve 304 are covered with endothelium.

Figures 4, 4A:
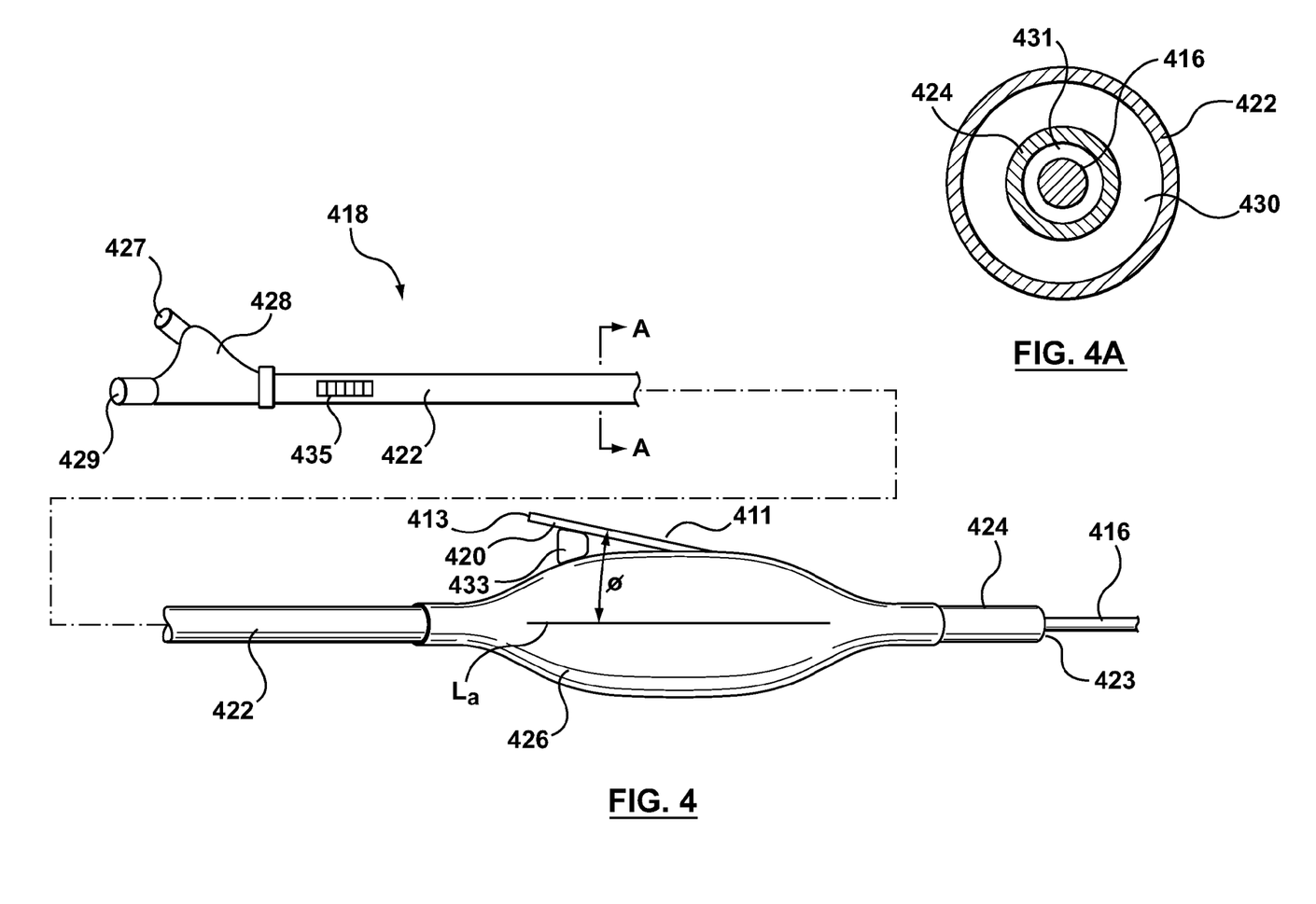
FIG. 4 is a side view of a balloon catheter in accordance with an embodiment hereof.
FIG. 4A is a cross-sectional view of the balloon catheter of FIG. 4 taken along line A-A.

FIGS. 4 and 4A depict a balloon catheter 418 having a deployable dissecting blade 420 thereon for forming a venous valve from autologous tissue according to an embodiment hereof. Balloon catheter 418 includes a tubular component or outer shaft 422, an inner guidewire shaft 424, and an inflatable balloon 426 positionable at a target location within the vasculature. Balloon 426 is shown in an expanded or inflated configuration in FIG. 4. Outer shaft 422 has a proximal end that extends out of the patient and is coupled to a hub 428, and a distal end coupled to a proximal end of balloon 426. Guidewire shaft 424 is attached to hub 428 and terminates distally of balloon 426, defining a distal guidewire port 423. In an embodiment, guidewire shaft 424 may be a flexible tube of a polymeric material, such as, e.g., polyethylene tubing. In the coaxial catheter construction of the illustrated embodiment, guidewire shaft 424 extends within outer shaft 422 such that an annular inflation lumen 430 is defined between an inner surface of outer shaft 422 and an outer surface of guidewire shaft 424. Other types of catheter construction are also amendable to the invention, such as, without limitation thereto, a catheter shaft formed by multi-lumen profile extrusion. Inflation lumen 430 allows inflation fluid received through an inflation port 427 of hub 428 to be delivered to balloon 426. As would be understood by one of ordinary skill in the art of balloon catheter design, hub 428 provides a luer hub or other type of fitting that may be connected to a source of inflation fluid and may be of another construction or configuration without departing from the scope of the present invention. In addition, hub 428 includes a guidewire port 429 that communicates with a guidewire lumen 431 of guidewire shaft 424 for receiving a guidewire 416 there through.

Figure 5:
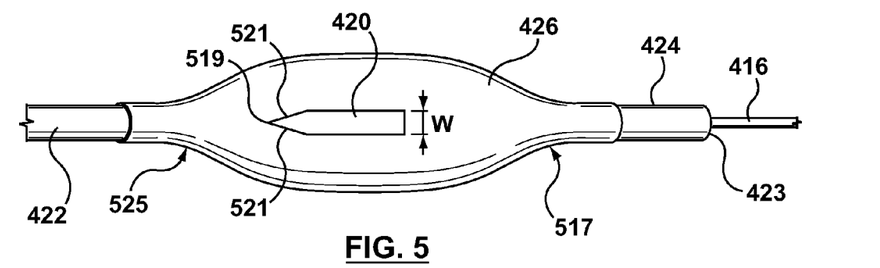
FIG. 5 is another side view of a distal portion of the balloon catheter of FIG. 4 rotated 90° from the position shown in FIG. 4.
Figure 5A:
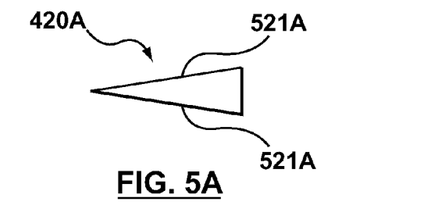
FIG. 5A-5D are top views of alternative dissecting blade configurations in accordance with embodiments hereof.
Figure 5B:
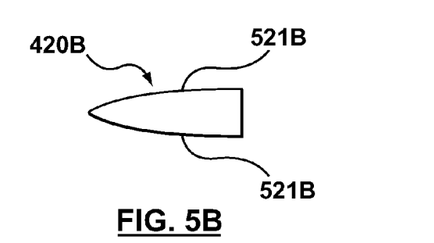
Figure 5C:
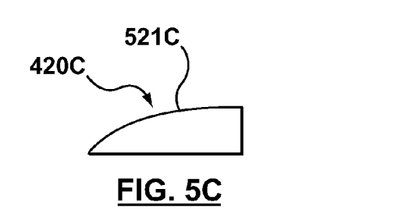
Figure 5D:
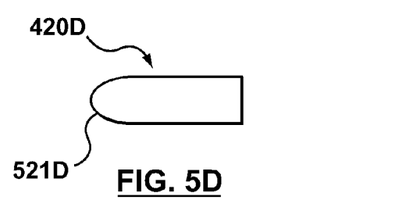

FIG. 5 is a side view of balloon 426 having deployable dissecting blade 420 thereon. As described in more detail herein with respect to FIGS. 6-10, dissecting blade 420 is utilized to dissect an intimal flap of tissue from a vein wall to create a new monocuspid venous valve of native tissue. Although shown with only one dissecting blade 420 mounted thereon, catheter 418 may be constructed with two or three dissecting blades positioned around the circumference of balloon 426, as shown in FIGS. 5F and 5G respectively, to create corresponding, bicusp or tricusp leaflets as will be described in more detail herein. Further, the location of dissecting blade 420 on balloon 426 is not limited to the longitudinal position illustrated in FIGS. 4 and 5, such that in other embodiments hereof dissecting blade 420 may be positioned at another longitudinal position along balloon 426 to include being positioned on or adjacent to a proximal end 525 of balloon 426 or a distal end 517 of balloon 426.

Figure 5E:
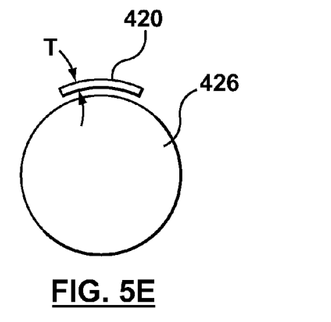
FIG. 5E is an end view of FIG. 5, showing the distal portion of the balloon catheter.
Figure 5F:
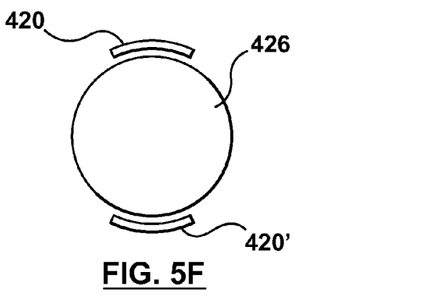
FIGS. 5F-5G are end views of balloons having two and three blade configurations, respectively, in accordance with embodiments hereof.
Figure 5G:
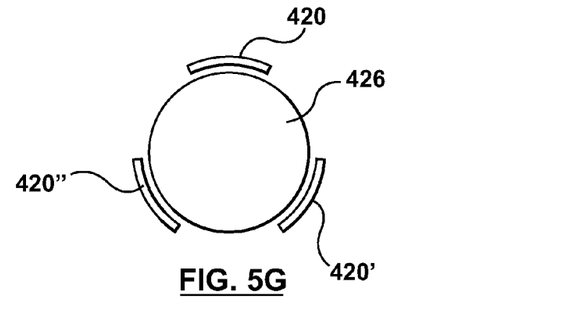

In the embodiment depicted in FIG. 5, dissecting blade 420 has a generally rectangular base portion and a generally triangular tip portion and as shown in FIG. 5E has a curved cross-section that substantially corresponds to the curve of the outer surface of inflated balloon 426. In one embodiment, dissecting blade 420 may have a width W that ranges between 2-3 mm, a thickness T that ranges between 0.20 and 0.40 mm, and a length that ranges between 8-10 mm.

The generally triangular tip portion includes two sharp lateral cutting edges 521 operable to cleanly cut or slice within the intima of a vessel wall, resulting in a lateral cut or subintimal longitudinal dissection that separates intimal tissue from medial tissue as will be described in more detail herein. Lateral cutting edges 521 extend in a proximal direction, i.e., towards proximal end 525 of balloon 426, longitudinally tapering to a tip 519 to result in the generally triangular tip portion of dissecting blade 420. In order to perform the dissection, tip 519 may be pointed or sharpened such that dissecting blade 420 will more readily slice through the tissue. In one embodiment, cutting edges 521 may be beveled edges forming an approximately 45 degree slope between the side surfaces or faces of blade 420. In other embodiments, cutting edges 521 of blade 420 do not include a bevel. When a protective sheath is used to cover dissecting blade 420 during advancement through the vasculature to the target site, the longitudinal edges of curved dissecting blade 420 conform to the outer surface of balloon 426 to shield the vasculature from unintentional vessel damage. In addition, the curved cross-section of blade 420 may be beneficial when dissecting the intimae from the curved vessel wall in that the curved nature may require a shorter distance cut into the vessel wall for creating an intimal flap of tissue of appropriate length from a vein wall. In another embodiment, the dissecting blade may have a rectangular or other non-curved cross-section.

As will be apparent to one of ordinary skill in the art, blade 420 is not limited to the configuration depicted in FIG. 5. Other configurations of blade 420 are contemplated, such as for example a generally triangular dissecting blade 420A having two cutting edges 521A that longitudinally taper to a sharpened tip 519A as shown in FIG. 5A, a spatula or bullet-shaped dissecting blade 420B having two cutting edges 521B as shown in FIG. 5B, a knife-shaped dissecting blade 420C having only one cutting edge 521C as shown in FIG. 5C, and a scoop or rounded dissecting blade 420D having only one rounded cutting edge 521D as shown in FIG. 5D. Dissecting blade 420 may be formed from any material suitable to penetrate into a vein wall and to separate intima and/or media tissue of the vein wall from remaining tissue of the vein wall. For example, dissecting blade 420 may be formed from stainless steel, a nickel-titanium alloy (nitinol), a relatively hard and sharp polymer, or a relatively hard and sharp ceramic material.

The blades of the devices described herein can incorporate different materials for improved functionality. In one embodiment, radiopaque markers are attached to the blade and separated by a defined distance. The radiopaque markers are selected from materials having a different radiopacity than the blade; such materials include but are not limited to platinum and gold. In one embodiment, the markers are small discs that are approximately 1 mm in diameter and have a thickness in the range of 0.010" to 0.020". These marker discs can be attached to the blade using several techniques including but not limited to: solder, welding, adhesive, press-fit. The markers can be spaced at a distance such that they can be readily distinguished from each other using fluoroscopy or other known imaging methods (e.g. 1 mm increments). In other embodiments the markers can be bands or have some shape other than a disc shape. Under fluoroscopy, the markers would allow a clinician to determine how far the blade had advanced into the vein wall.

A distal end 411 of dissecting blade 420 is coupled to balloon 426 to allow a proximal end 413 of blade 420 to extend away unattached from balloon 426 at an angle Ø relative to the longitudinal axis $L_a$ of balloon 426 such that proximal end 413 of dissecting blade 420 is radially spaced from the outer surface of balloon 426. Blade 420 extends from balloon 426 at angle Ø in order to penetrate the vein wall to create a longitudinal dissection of intimal tissue after balloon 426 is inflated and manipulated as discussed further below. The angle between dissecting blade 420 and balloon 426 is limited to a certain or predetermined angle Ø that has been selected to prevent dissecting blade 420 from entering the vein wall at an inappropriate angle, such as an angle that would create too thick a dissection or worse would direct the blade entirely through the vein wall. Predetermined angle Ø is an inclined or acute angle and may range from 5°-60°. In one embodiment, predetermined angle Ø is approximately 30 degrees. In such embodiments, dissecting blade 420 and balloon 426 may be coupled together at angle Ø.

Figure 13:
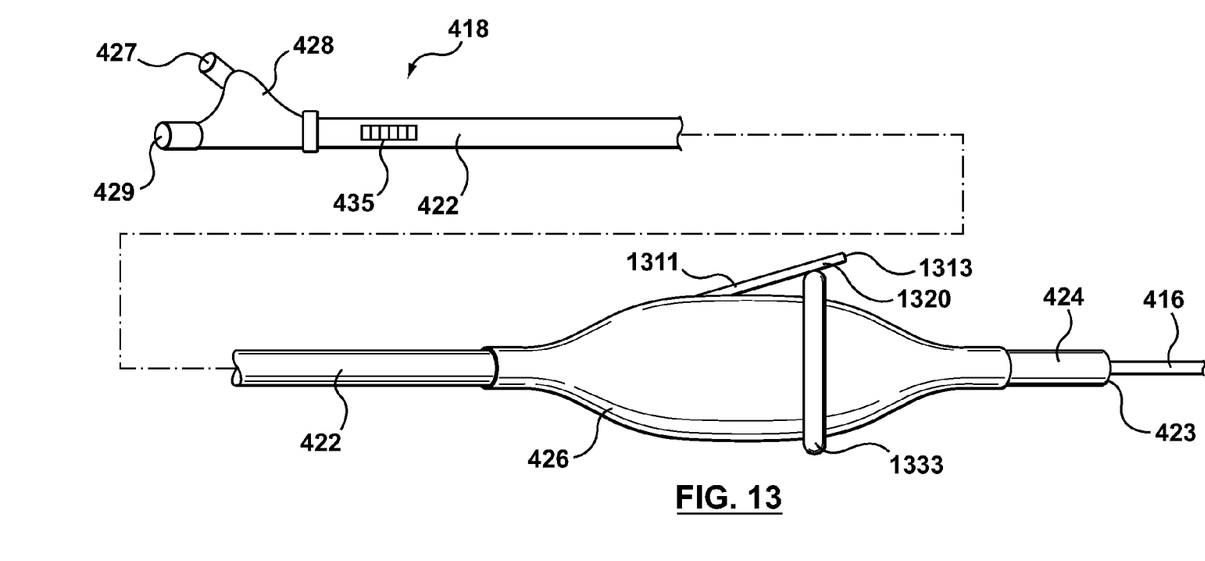
FIG. 13 is a side view of a balloon catheter having a distally-extending dissecting blade thereon in accordance with another embodiment hereof.

In order to limit the angle between dissecting blade 420 and longitudinal axis $L_a$, viz., balloon 426, a small ramp 433 may be coupled to or formed in the outer surface of balloon 426 underneath proximal end 413 of blade 420 to direct dissecting blade 420 at predetermined angle Ø. In an embodiment, ramp 433 may be a wedge of any suitable material that fixes angle Ø between dissection blade 420 and balloon 426. In another embodiment, ramp 433 may be an inflatable pillow such that angle Ø between dissection blade 420 and balloon 426 is adjustable or variable via inflation pressure. As the inflatable pillow radially expands, it pushes or elevates proximal end 413 of blade 420 to an angle Ø that can be controlled and guided under ultrasonography or other suitable imaging method. The height of ramp 433 is thus adjustable in situ to vary angle Ø at which blade 420 extends from balloon 426. The inflatable pillow may be in fluid communication with inflation lumen 430 such that inflation of balloon 426 also expands the inflated pillow, or the inflatable pillow may be in fluid communication with a separate inflation lumen (not shown) extending through balloon catheter 418 such that the inflatable pillow can be deployed independently of balloon 426. In yet another embodiment, ramp 433 may be an annular inflatable ring (shown in FIG. 13 as element 1333) that encircles the outer surface of balloon 426 at a longitudinal location along balloon 426 such that a portion of the annular ring extends underneath proximal end 413 of blade 420. Advantageously, an annular ramp would simultaneously angle all blades attached to balloon 426 if a bicuspid or tricuspid valve is being created as described herein with respect to FIGS. 5F and 5G. Similar to the inflatable pillow ramp embodiment, an annular inflatable ring is inflatable and thus angle Ø between dissection blade 420 and balloon 426 is adjustable or variable via inflation pressure. The annular inflatable ring may be in fluid communication with inflation lumen 430 such that inflation of balloon 426 also expands the ring, or the ring may be in fluid communication with a separate inflation lumen (not shown) extending through balloon catheter 418 such that the ring can be deployed independently of balloon 426. In another embodiment, an elongated wire (not shown) may be attached to distal end 411 of blade 420 and extend through the length of balloon catheter 418 such that a proximal end of the wire may be manipulated by the clinician. Blade 420 initially lays flat against the outside surface of balloon 426, with the elongated wire therebetween. When it is desired to "deploy" blade 420 such that it extends from balloon 426 at angle Ø, the clinician pulls the elongated wire in order to cause proximal end 413 of blade 420 to flip outwards or radially extend from balloon 426. Further, by pulling on the wire in a controlled and coordinated manner, angle Ø may be adjusted in situ.

In the embodiment shown in FIGS. 4 and 4A, balloon catheter 418 has an over-the-wire (OTW) catheter configuration. Any suitable balloon catheter configuration may be utilized. For example, in another embodiment, catheter 418 may be modified to be of a rapid exchange (RX) catheter configuration without departing from the scope of the present invention such that guidewire shaft 424 extends within only the distal portion of catheter 418. In such an embodiment, a proximal portion of outer shaft 422 may include a metal hypotube with a guidewire transition area having a proximal guidewire port being positioned proximal of balloon 426 approximately 20 cm to 25 cm.

Outer shaft 422 may be formed of a polymeric material, non-exhaustive examples of which include polyethylene, PEBA (PEBAX), polyamide and/or combinations thereof, either blended or co-extruded. Optionally, outer shaft 422 or some portion thereof may be formed as a composite having a reinforcement material incorporated within a polymeric body in order to enhance strength and/or flexibility. Suitable reinforcement layers include braiding, wire mesh layers, embedded axial wires, embedded helical or circumferential wires, and the like. In one embodiment, for example, at least a proximal portion of outer catheter shaft 422 may be formed from a reinforced polymeric tube.

Figure 6:
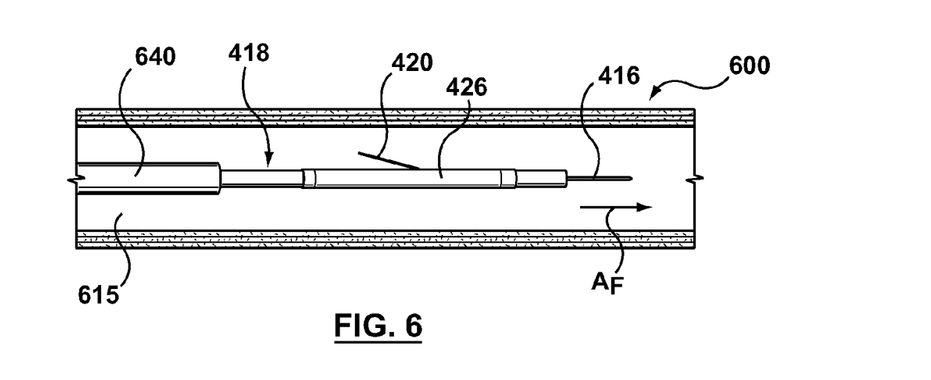
FIGS. 6-10 are schematic representations of a method of forming a venous valve from autologous tissue in accordance with an embodiment hereof.

FIGS. 6-10 are schematic representations of a method of forming a venous valve from autologous tissue in accordance with an embodiment hereof, wherein the method includes utilizing dissecting blade 420 to create at least one flap in a vein which then acts as a one-way valve in the manner of a native venous valve. Dissecting blades described herein may be delivered to the target site in an antegrade manner. Antegrade delivery allows the dissecting blade to pass through the native valves without incidental damage thereto. In one embodiment, percutaneous luminal access to a desired peripheral vein 600 is obtained through the popliteal vein or posterior tibial vein in the lower leg and delivery of the dissecting blade is in an antegrade direction such that the dissecting blade passes forwardly (i.e., distal to proximal relative to the heart) through native valves located within the vein in route to a target location where a new vein valve is to be created. In other embodiments, luminal access to desired peripheral vein 600 is obtained through the greater or lesser saphenous, femoral, or popliteal veins using standard percutaneous techniques. It should be understood by one of skill in the art that methods as described herein may be used to form an autologous valve in any vein of sufficient thickness to enable a dissection to occur as described in greater detail below. Initially guidewire 416 is maneuvered through the vasculature to rest across a target location within lumen 615 of vein 600 where a new venous valve is to be created. Balloon catheter 418 having deployable dissecting blade 420 located thereon is then advanced in an antegrade direction, i.e., in the direction of antegrade flow $A_F$, over guidewire 416 to the target location. If desired, a protective sheath 640 may be provided to surround balloon 426 and cover dissecting blade 420 until deployment to facilitate tracking of balloon catheter 418 over guidewire 416 through the vasculature and prevent unintentional vessel damage while advancing dissecting blade 420 to the target site. FIG. 6 illustrates balloon catheter 418 positioned at the target site, with balloon 426 in a delivery or non-inflated configuration and sheath 640 partially retracted, such that dissecting blade 420 protrudes from balloon 426 at angle Ø as described with reference to FIG. 4.

Figure 7:
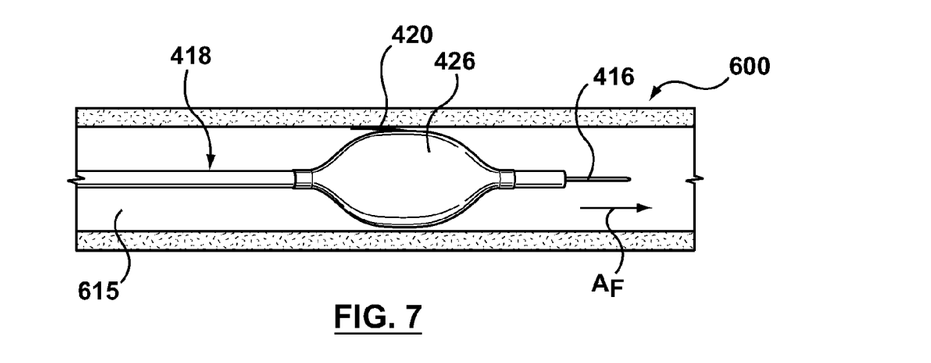

Once positioned as shown in FIG. 6, inflation fluid is provided via inflation port 427 (shown in FIG. 4) of hub 428 so that balloon 426 may be inflated as is known to one of ordinary skill in the art. As shown in FIG. 7, balloon 426 of catheter 418 is inflated to such an extent that at least a point or proximal portion of dissecting blade 420 is deployed against the vascular wall of the vessel, i.e., fully positioned against or makes contact with the vessel wall.

Figure 8:
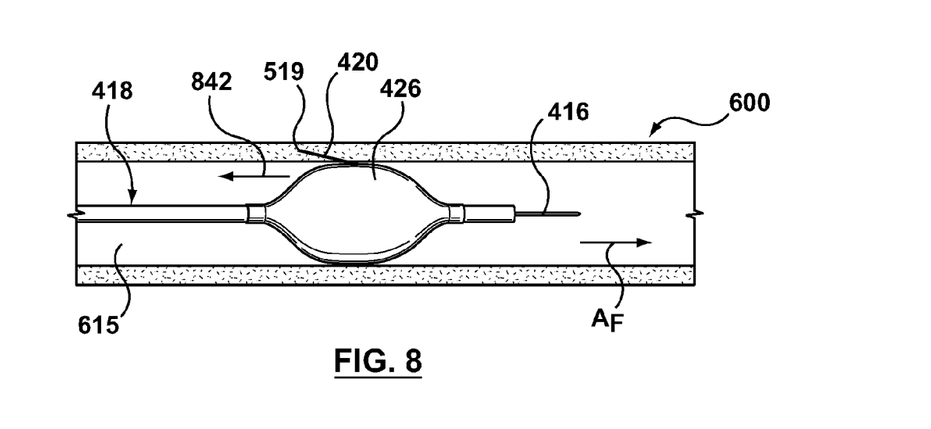

After balloon expansion, catheter 418 is slightly proximally retracted in a direction indicated by arrow 842. Since cutting edges 521 of blade 420 extend in a proximal direction, retraction of catheter 418 causes dissecting blade 420 to puncture or pierce the intimal layer of the wall of vein 600. As shown in FIG. 8, pointed tip 519 of dissecting blade 420 is proximally retracted a sufficient distance to create a subintimal longitudinal dissection of the intimal layer that separates tissue of the vein wall that substantially parallels a longitudinal axis of vein 600. The subintimal longitudinal dissection may longitudinally extend within the intimal layer, between the intimal layer and the medial layer, between the medial layer and the adventitial layer, or within the medial layer; with care being taken that dissecting blade 420 does not pass entirely through the vein wall.

Fluoroscopic or ultrasonographic guidance of retracting catheter 418 may be utilized to assure a length of the dissection plane created within the vein wall, as a length of the dissection plane will determine a length of the resulting flap. In order to make a monocuspid flap, the flap must have a free edge length of greater than half of the circumference of the vessel lumen with the depth of the dissection plane being sufficient to allow the resulting flap to touch the opposite side of the vessel wall. In order to make a bicuspid flap, each flap must have a free edge length of roughly half of the circumference of the vessel lumen with the depth of each dissection plane being sufficient to allow the resulting flaps to touch one another in the centerline of the vessel lumen. In order to determine an accurate depth/length of the dissection plane, an accurate measurement of the diameter of the vessel may be obtained by using fluoroscopy and quantitative coronary angiography (QCA). In such a procedure, the clinician uses a software/video tool to "mark" the monitor with the fluoroscopic image. The tool has a calibrated measurement system so the clinician can accurately measure the diameter of the vein. Further, vessel diameter and wall thickness measurements may be obtained via intravascular ultrasound (IVUS), a medical imaging methodology that utilizes a miniaturized ultrasound probe attached to a distal end of a catheter to see from inside blood vessels out through the surrounding blood column. IVUS allows visualization of the inner wall of the vessel and thus the clinician may watch blade 420 creating the dissection in real time. Alternatively, angiography with a road map may also be utilized to watch the vessel in real time, which may be augmented by the inclusion of radiopaque markers on balloon catheter 418 and/or blade 420.

In addition, a series of depth markers 435 (see FIG. 4) may be located on the proximal portion of outer shaft 422 that extends outside of the patient's body in order to aid the physician in assessing how much to proximally retract catheter 418 to ensure that the appropriate length of tissue is dissected. Series of markers 435 may be spaced apart at predefined increments. Such predefined increments could be in the range of 1.0 to 5.0 mm. The location or position of the series of markers 435 on outer shaft 422 relative to a stationary object, such as a proximal hub of a guide catheter or sheath, may be monitored by the physician to track or measure how far catheter 418 is retracted during the cutting step of the procedure, thereby monitoring the length or depth of the dissection performed by blade 420 situated near the distal end of catheter 418. The series of markers 435 may be printed on outer shaft 422 using pad-printing, laser printing, etching, or other common printing techniques. Another method to monitor the length of the dissection includes placing a single marker such as an O-ring over the proximal portion of catheter 418. The single marker may be placed adjacent to or abutting against the insertion point of catheter 418 prior to performance of the dissection step. As catheter 418 is proximally retracted in order to create a dissection plane within the vein wall, the distance between the marker and the insertion point is monitored and measured (using suitable measuring devices) to track the length of the dissection being formed by blade 420. Visualization tools and methods that are suitable for use with the devices and methods for creating native tissue venous valves disclosed here include, but are not limited to, angiography, IVUS, duplex ultrasound, optical coherence tomography, and other known imaging technologies either alone or in combination.

Figure 9:
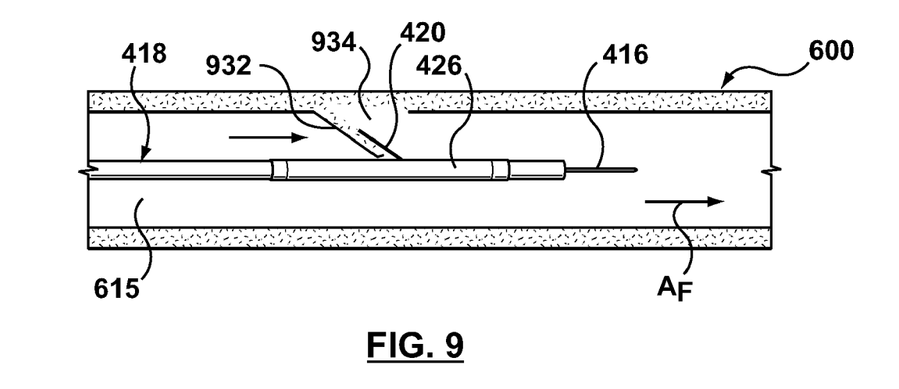

To complete the formation of the new venous valve after the dissection has been created in the vein wall, balloon 426 is subsequently deflated such that the dissecting blade 420 pulls or directs a flap 932 of tissue towards lumen 615 of vein 600 as shown in FIG. 9. The width W of dissecting blade 420, as well as the fact that blade 420 extends from balloon 426 at angle Ø, causes flap 932 of tissue to pull away from the vessel wall as balloon 426 is deflated to a smaller profile. Stated another way, deflation of balloon 426 essentially peels flap 932 of tissue away from the remaining tissue of the vein wall via blade 420. A flap by definition is a moveable piece of tissue partly connected to the body, and accordingly, it should be understood by the preceding description that a distal end of flap 932 remains connected to the remaining tissue of vein 600 while a proximal end or edge of the flap 932 is dissected away from the remaining tissue of the vein wall. When dissecting blade 420 pulls flap 932 of tissue towards lumen 615 of vein 600, a pocket or sinus 934 is simultaneously formed between flap 932 and the remaining tissue of the vein wall. Sinus 934 has a conical or tapered shape in which a distal diameter thereof is smaller than a proximal diameter thereof. The tapered shape of pocket or sinus 934, which mimics a native valve sinus, aids in permitting blood to fill pocket 934 and close flap 932. As mentioned previously, when referring to flap 932 of tissue and other features of the venous valve, the term "proximal" refers to the end closest to the heart by way of blood flow path while the term "distal" refers to the end away from the heart by way of blood flow path.

Figure 10:
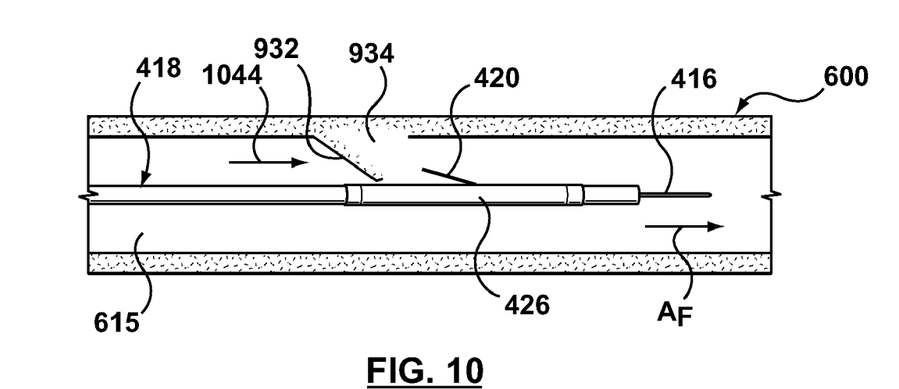

In order to remove balloon catheter 418, catheter 418 is distally advanced in a direction indicated by arrow 1044 to disengage dissecting blade 420 from flap 932 as shown in FIG. 10. Balloon catheter 418 and guidewire 416 may then be proximally retracted and removed from the patient. If desired, sheath 640 may be re-advanced over dissecting blade 420 prior to proximally retracting and removing balloon catheter 418 from the patient. Another embodiment is configured with a sheath that is pushed distally from the operation clinician (using for example a wire that moves through the catheter and is attached to the distal end of the sheath); such that as the sheath moves off of the blade, it also moves toward the distal end of the balloon. Once the procedure is completed, the sheath is moved proximally toward the clinician and it collapses the blade against the balloon. In another embodiment, the blade is secured to the ramp/inflation ring; such that when the balloon is deflated after a procedure, the blade rests snugly against the surface of the balloon to facilitate a sheath being replaced over the blade.

Figure 11A:
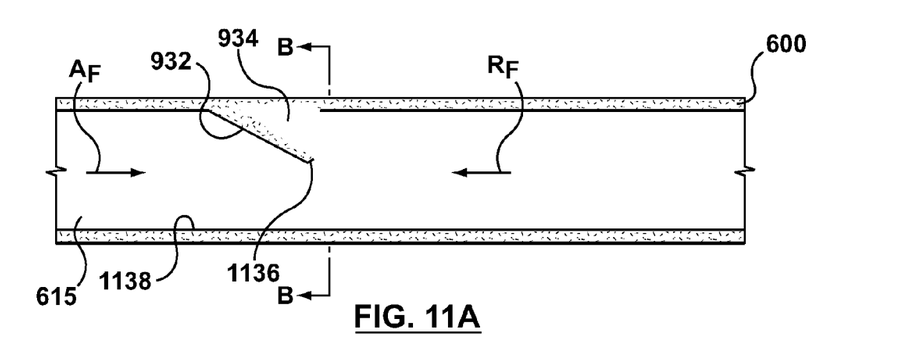
FIG. 11A is a schematic representation of a monocuspid venous valve formed in accordance with embodiments hereof.
Figure 11B:
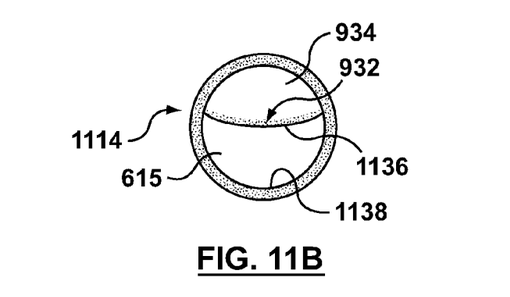
FIG. 11B is a cross-sectional view of FIG. 11A taken along line B-B.

In the embodiment of FIGS. 11A and 11B, flap 932 includes a free edge 1136 of a sufficient length to make contact with an opposing side 1138 of the vein wall of lumen 615, such that in the absence of antegrade blood flow, represented by arrow $A_F$, free edge 1136 seals against opposing side 1138 while retrograde or gravitational blood flow, represented by arrow $R_F$, fills pocket 934. When antegrade blood flow $A_F$ is once again present in vein 600, and a pressure gradient exists such that $A_F > R_F$, flap 932 is pushed away from opposing side 1138, as shown in FIG. 11B, to allow blood flow through new venous valve 1114 on its way back to the heart. In such an embodiment, flap 932 and pocket 934 constitute a one-way monocuspid or one-leaflet venous valve 1114 of autologous tissue. Further, even if flap 932 is not of a sufficient length to fully extend across lumen 615 and seal against opposing side 1138 of the vein wall, the presence of flap 932 and pocket 934 will significantly reduce the amount of blood that can reflux or backflow down the vessel.

Figure 11C:
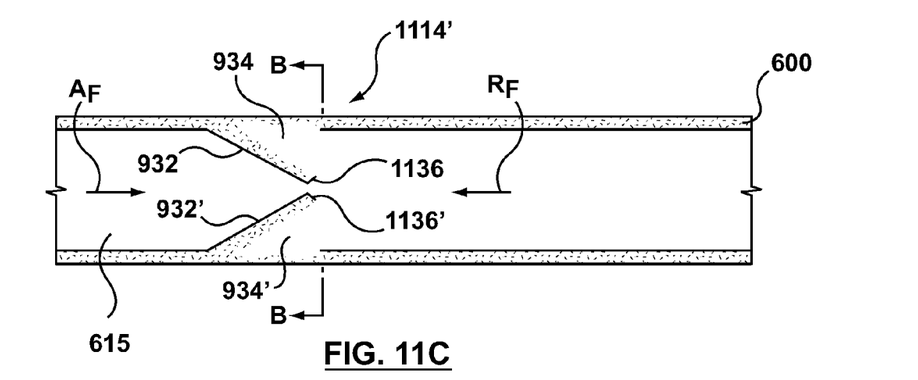
FIG. 11C is a schematic representation of a bicuspid venous valve formed in accordance with embodiments hereof.
Figure 11D:
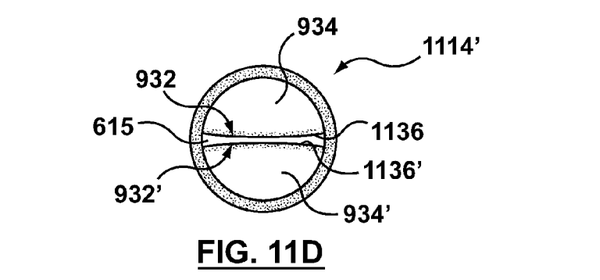
FIG. 11D is a cross-sectional view of FIG. 11C taken along line D-D.

In another embodiment hereof illustrated in FIG. 5F, an additional or second dissecting blade 420' may be positioned on balloon 426 approximately 180 degrees from dissecting blade 420 in order to simultaneously form a second flap 932' and a second pocket 934' at an opposed location within vein 600, as shown in FIGS. 11C and 11D. Such an embodiment forms a bicuspid or two-leaflet venous valve 1114' where free edges 1136, 1136' meet to close lumen 615 in the absence of antegrade blood flow $A_F$ when retrograde blood flow $R_F$ fills pockets 934, 934'. In another embodiment illustrated in FIG. 5G, a total of three dissecting blades 420, 420', and 420" may be positioned on balloon 426 at equally-spaced radial positions around the circumference of balloon 426 in order to simultaneously form a tricuspid or three-leaflet valve.

It is also possible to create bicuspid and tricuspid valves using a device having a single blade as described above. When using a single blade device, the catheter is rotated after creating each flap until the desired number of flaps is created. The device can include a marker that allows a clinician to measure the rotation of the blade inside the vein such that it will not damage a previously created flap.

Figures 12, 12A, 12B:
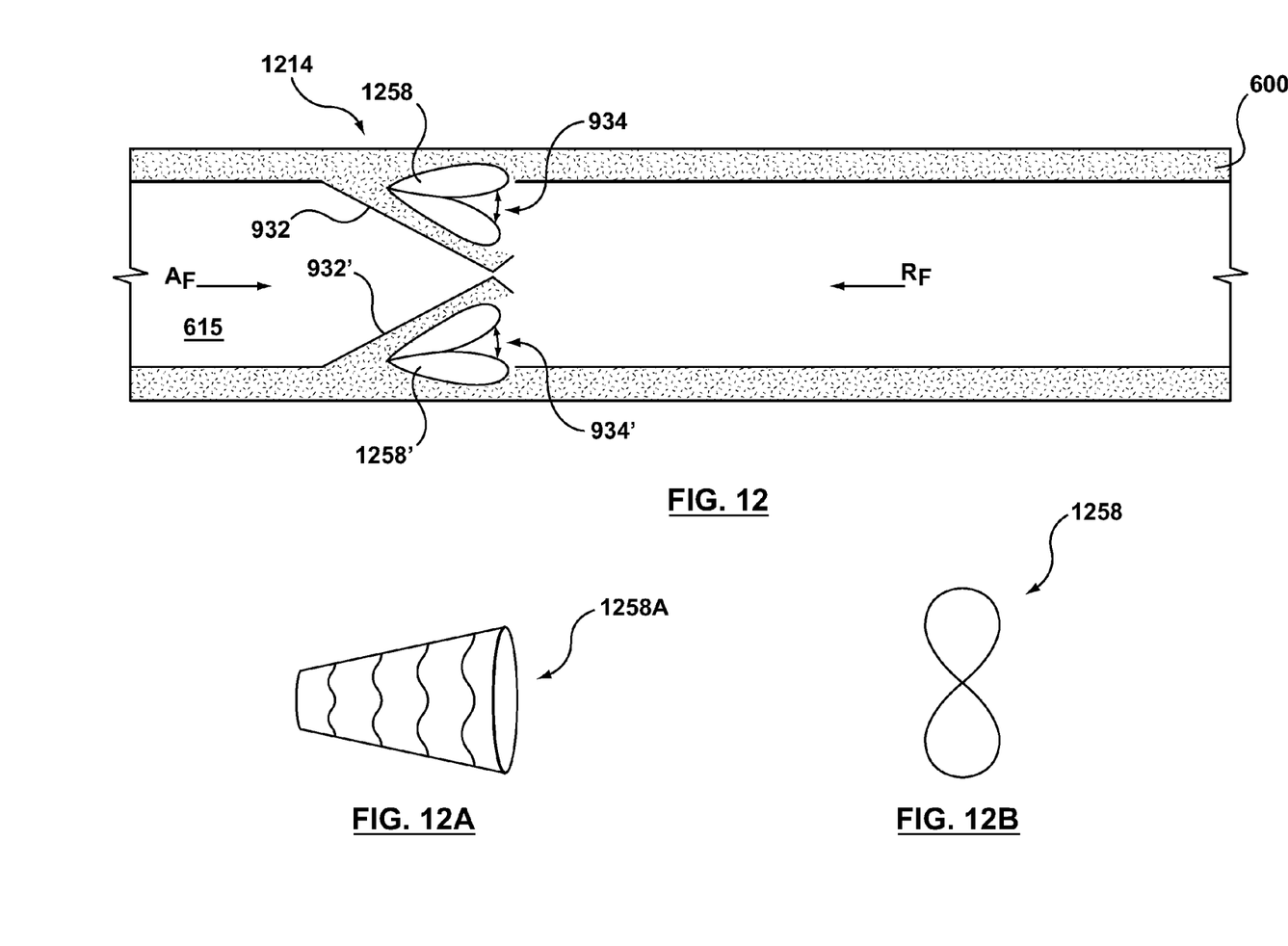
FIG. 12 is a schematic representation of the bicuspid venous valve of FIG. 11C including biasing elements in accordance with embodiments hereof.
FIG. 12A is a schematic representation of a tapered stent for use in venous valves formed in accordance with embodiments hereof.
FIG. 12B is a schematic representation of a biasing element for use in venous valves formed in accordance with embodiments hereof.

In each of the aforementioned embodiments, the dissected flaps 932, 932' provide the same internal, i.e., facing the blood flow, tissue structure as a native valve thus providing a distinct advantage over prosthetic valve approaches. If the newly created flaps or leaflets 932, 932' do not exhibit enough structural integrity to take the shape of a cusp or leaflet or if the flaps remain adhered to the remaining tissue of the vein wall the performance of those structures may be supplemented via biasing elements placed into pockets 934, 934'. The biasing elements are designed to hold the shape of the pockets and do not offer much resistance to antegrade blood flow but instead collapse and allow the valve to open in the presences of antegrade flow. More particularly, with reference to FIG. 12, spring clip devices 1258, 1258' may be placed into first and second pockets 934, 934' to aid in completely closing vessel lumen 615 in the absence of antegrade blood flow $A_F$ by biasing first and second flaps 932, 932' against one and other. In this manner, retrograde blood flow $R_F$ is impeded from seeping through free edges 1236, 1236' and causing reflux to instead fill first and second pockets 934, 934'. When antegrade blood flow $A_F$ once again pushes upon first and second flaps 932, 932', spring clip devices 1258, 1258' are compliant enough to compress to allow first and second flaps 932, 932' to part such that antegrade blood flows through bicuspid valve 1214. Spring clip devices 1258, 1258' would be percutaneously delivered. In an embodiment the spring clips may be manufactured from a superelastic material such as nitinol. The clips may be shaped into a FIG. 8, as shown in FIG. 12B, and then folded at the mid-point to an appropriate angle, as shown in FIG. 12. In an embodiment, a suitable range for this angle is between 20 to 60 degrees. The spring-clip may be shape-set into this configuration using an oven set to an appropriate temperature for the material, by e.g., 525° C. for nitinol. The spring clip would then be loaded into a catheter assembly at the distal tip and advanced to the tissue pockets (sinus) in a retrograde direction. A pusher rod or other delivery mechanism may then be used to push the spring-clip out of the distal tip of the catheter and into the tissue pocket. Because of the materials superelasticity, the spring clip will self-expand to its original folded FIG. 8 configuration. Thus the material would contact the inner edge of the vessel wall and the inner edge of the created tissue pocket. In another embodiment, a tapered compliant stent 1258A as shown in FIG. 12A may be placed in each of first and second pockets 934, 934' to function in the same manner as previously described for spring clip devices 1258, 1258'. Compliant stent 1258A may be made of nitinol with a very thin wall, such as having a wall thickness of between 0.001 to 0.005 inch.

Figure 14:
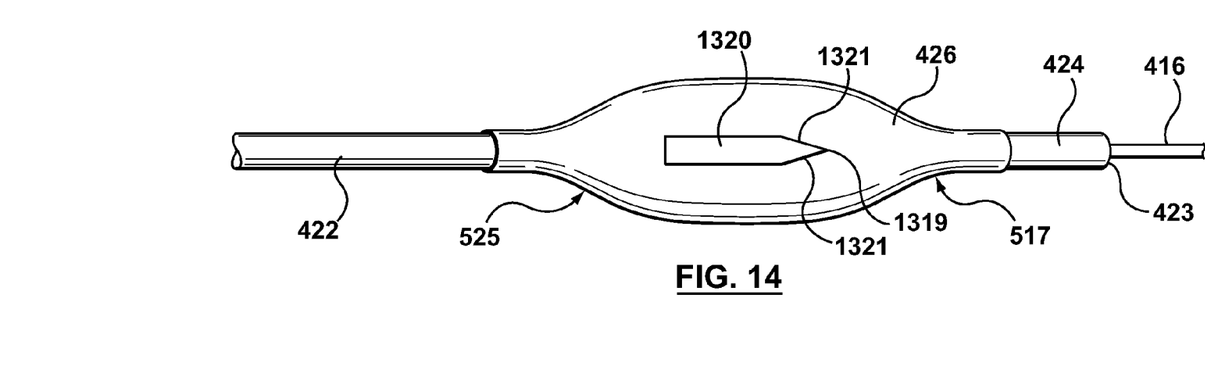
FIG. 14 is another side view of a distal portion of the balloon catheter of FIG. 13 rotated 90° from the position shown in FIG. 13.

Although embodiments hereof have been described for delivering in an antegrade manner, it will be apparent to those of ordinary skill in the art that the systems and methods described herein may be adapted for delivery in a retrograde manner. For example, referring to FIG. 13, balloon catheter 418 is shown having a deployable dissecting blade 1320 thereon for forming a venous valve from autologous tissue in a retrograde manner according to an embodiment hereof. FIG. 14 is another side view of balloon 426 having deployable dissection blade 1320 thereon. Dissecting blade 1320 may have the same configurations described above with respect to blade 420 for dissecting an intimal flap of tissue from a vein wall, but lateral cutting edges 1321 extend in a distal direction, i.e., towards distal end 517 of balloon 426, longitudinally tapering to a tip 1319. A proximal end 1311 of dissecting blade 1320 is coupled to balloon 426 to allow a distal end 1313 of blade 1320 to radially extend away from balloon 426 at an angle Ø relative to the longitudinal axis $L_a$ of balloon 426 such that distal end 1313 of dissecting blade 1320 is radially spaced from the outer surface of balloon 426. In this embodiment, an annular inflatable ring 1333 encircles the outer surface of balloon 426 at a longitudinal location along balloon 426 such that a portion of the annular ring extends underneath distal end 1313 of blade 1320 in order to angle the distal end of dissecting blade 1320 from balloon 426.

When creating an intimal flap of tissue in a retrograde manner, the method of use is essentially the same as described above in FIGS. 6-10 for an antegrade approach with a few variations. Balloon catheter 418 having deployable dissecting blade 1320 located thereon is advanced in a retrograde direction, i.e., in the direction of retrograde flow $R_F$, over guidewire 416 to the target location. Once positioned, a delivery sheath or other covering is refracted to expose dissecting blade 1320 and the balloon is inflated to deploy blade 1320 against the vascular wall of the vessel. After balloon expansion, catheter 418 is slightly distally advanced or pushed forward. Since cutting edges 1321 of blade 1320 extend in a distal direction, forward advancement of catheter 418 causes dissecting blade 1320 to puncture or pierce the intimal layer of the wall of the vein. Catheter 418 is advanced a sufficient distance to create a subintimal longitudinal dissection of the intimal layer that separates tissue of the vein wall that substantially parallels a longitudinal axis of the vein. To complete the formation of the new venous valve, balloon 426 is deflated such that the dissecting blade 1320 pulls or directs a flap of tissue towards the lumen of the vein, simultaneously forming a pocket or sinus between the flap and the remaining tissue of the vein wall. Catheter 418 having blade 1320 thereon is then proximally retracted to disengage dissecting blade 1320 from the flap and is further retracted to remove catheter 418 from the patient. As discussed above, the sheath can be placed over the blade when the catheter is retracted from the patient.

While various embodiments hereof have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope hereof should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A percutaneous method for creating a venous valve from autologous tissue, the method comprising the steps of:
   advancing a balloon catheter to a target site, wherein the balloon catheter includes a balloon having at least one dissecting blade coupled to the balloon;

inflating the balloon of the balloon catheter to deploy the at least one dissecting blade against a wall of a vein;

longitudinally translating the balloon catheter such that the at least one dissecting blade penetrates into the vein wall and forms a subintimal longitudinal dissection of at least intimal tissue of the vein wall that is separated from remaining tissue of the vein wall;

deflating the balloon of the balloon catheter such that the at least one dissecting blade separates the subintimal longitudinal dissection of tissue from the remaining tissue of the vein wall and pulls the subintimal longitudinal dissection of tissue into a lumen of the vein and thereby simultaneously forms a flap of tissue and a sinus between the flap and the remaining tissue of the vein wall, wherein the flap and the sinus constitute at least a portion of the venous valve.

2. The method of claim 1, further comprising the step of:
advancing the balloon catheter to disengage the at least one dissecting blade from the flap of tissue after deflating the balloon of the balloon catheter.

3. The method of claim 1, wherein the balloon has one dissecting blade coupled to the balloon and a free edge of the flap is of a length that is greater than half the circumference of the vein lumen to form a monocuspid leaflet of the venous valve.

4. The method of claim 3, wherein a depth of the subintimal longitudinal dissection is of sufficient length to allow the free edge of the flap to make contact with an opposing side of the vessel wall.

5. The method of claim 1, wherein the balloon has one dissecting blade coupled to the balloon and a free edge of the flap is of a length that permits the free edge of the flap to touch against an opposing wall of the vein to close a lumen of the vein in the absence of antegrade flow.

6. The method of claim 1, wherein fluoroscopic or ultrasonographic guidance is used while retracting the balloon catheter to determine a length of the subintimal longitudinal dissection plane created by the at least one dissecting blade.

7. The method of claim 1, wherein a proximal portion of the balloon catheter includes at least one marker that is utilized while retracting the balloon catheter to determine a length of the subintimal longitudinal dissection plane created by the at least one dissecting blade.

8. The method of claim 1, further comprising:
positioning a biasing element within the sinus to aid in holding the sinus open in the absence of antegrade blood flow to allow the sinus to fill with retrograde blood flow.

9. The method of claim 1, wherein the balloon catheter includes a balloon having first and second dissecting blades positioned on opposite sides of the balloon approximately 180 degrees from each other and wherein the first and second dissecting blades penetrate into the vein wall to create respective first and second subintimal longitudinal dissections in the vein wall so that at least intimal tissue of the vein wall is separated from remaining tissue of the vein wall and wherein deflating the balloon forms first and second flaps of tissue and first and second sinuses between the flaps and the remaining tissue of the vein wall, wherein the first and second flaps and first and second sinuses constitute a venous valve having bicuspid leaflets.

10. The method of claim 9, wherein a free edge of the first flap and a free edge of the second flap each have a length that permits the free edges of the first and second flaps to touch against each other to close the vein lumen in the absence of antegrade flow.

11. The method of claim 1, wherein the balloon catheter includes a balloon having first, second, and third dissecting blades positioned around the circumference of the balloon and wherein the first, second, and third dissecting blades penetrate into the vein wall to create respective first, second, and third subintimal longitudinal dissections in the vein wall so that at least intimal tissue of the vein wall is separated from remaining tissue of the vein wall and wherein deflating the balloon forms first, second, and third flaps of tissue and first, second, and third sinuses between the flaps and the remaining tissue of the vein wall, wherein the first, second, and third flaps and first, second, and third sinuses constitute a venous valve having tricuspid leaflets.

12. The method of claim 11, wherein the first, second, and third dissecting blades are approximately equally spaced around the circumference of the balloon.

13. The method of claim 1, wherein the balloon catheter is advanced in an antegrade manner via percutaneous access to the lumen of the vein and longitudinally translating the balloon catheter includes proximally retracting the balloon catheter.

14. The method of claim 13, wherein percutaneous access is obtained through a posterior tibial or popliteal vein in a lower leg.

15. The method of claim 1, wherein the at least one dissecting blade includes at least one marker thereon, and the marker has different radiopaque characteristics than the blade.

16. The method of claim 1, wherein the at least one dissecting blade includes a plurality of markers thereon,
the plurality of markers being evenly spaced along the blade;
and each marker has different radiopaque characteristics than the blade.

* * * * *